(12) United States Patent
Scharf

(10) Patent No.: US 9,432,763 B2
(45) Date of Patent: *Aug. 30, 2016

(54) WATER LEAK WARNING DEVICE

(71) Applicant: Joshua Scharf, Short Hills, NJ (US)

(72) Inventor: Joshua Scharf, Short Hills, NJ (US)

(73) Assignee: Widget Lab Inc., Short Hills, NJ (US)

( * ) Notice: Subject to any disclaimer, the term of this patent is extended or adjusted under 35 U.S.C. 154(b) by 57 days.

This patent is subject to a terminal disclaimer.

(21) Appl. No.: 14/488,722

(22) Filed: Sep. 17, 2014

(65) Prior Publication Data

US 2015/0003619 A1   Jan. 1, 2015

Related U.S. Application Data

(63) Continuation-in-part of application No. 13/837,759, filed on Mar. 15, 2013, now abandoned, which is a continuation-in-part of application No. 13/477,183, filed on May 22, 2012, now Pat. No. 8,970,386.

(60) Provisional application No. 61/488,914, filed on May 23, 2011.

(51) Int. Cl.
| | | |
|---|---|---|
| *G08B 21/00* | (2006.01) | |
| *H04R 1/28* | (2006.01) | |
| *G10K 15/08* | (2006.01) | |
| *G01M 3/16* | (2006.01) | |
| *B65D 1/00* | (2006.01) | |
| *A61B 1/00* | (2006.01) | |
| *G08B 21/20* | (2006.01) | |

(52) U.S. Cl.
CPC .............. *H04R 1/2807* (2013.01); *G01M 3/16* (2013.01); *G10K 15/08* (2013.01); *A61B 1/00* (2013.01); *B65D 1/00* (2013.01); *G08B 21/20* (2013.01)

(58) Field of Classification Search
CPC .................................. A61B 1/00; B65D 1/00
See application file for complete search history.

(56) References Cited

U.S. PATENT DOCUMENTS

| | | | |
|---|---|---|---|
| 3,597,263 A | 8/1971 | Bancroft | |
| 4,264,902 A * | 4/1981 | Miller | G08B 21/20 340/602 |
| 4,888,455 A | 12/1989 | Hanson | |
| 4,943,458 A | 7/1990 | Buecheler | |
| 5,072,948 A | 12/1991 | Kostrzewski | |
| 5,109,573 A * | 5/1992 | Sherman | E05C 17/025 16/341 |
| 6,524,857 B1 * | 2/2003 | Perkins | D06F 39/081 116/200 |
| 6,873,263 B1 * | 3/2005 | Hohman | G08B 21/20 340/602 |
| 2002/0033759 A1 | 3/2002 | Morello | |
| 2008/0255441 A1 | 10/2008 | Hadani | |
| 2009/0140866 A1 * | 6/2009 | Heilmann | G01M 3/186 340/605 |
| 2011/0048555 A1 | 3/2011 | Malouf | |

\* cited by examiner

*Primary Examiner* — Shirley Lu
(74) *Attorney, Agent, or Firm* — Gearhart Law LLC

(57) ABSTRACT

An easy-to-use, installation-free water leak warning device having a sturdy hollow body enclosing essential functioning elements including a power source, an amplifier, a speaker, and portions of two electrodes. The water leak warning device is preferably small in size and may be placed at potential water leak or flooding spots. The essential functioning elements are operatively connected with conductive material so that when leaked water flows to where the device is located, an audible signal can be emitted to remind the user of the device to prevent further leakage and mitigate any damage.

7 Claims, 14 Drawing Sheets

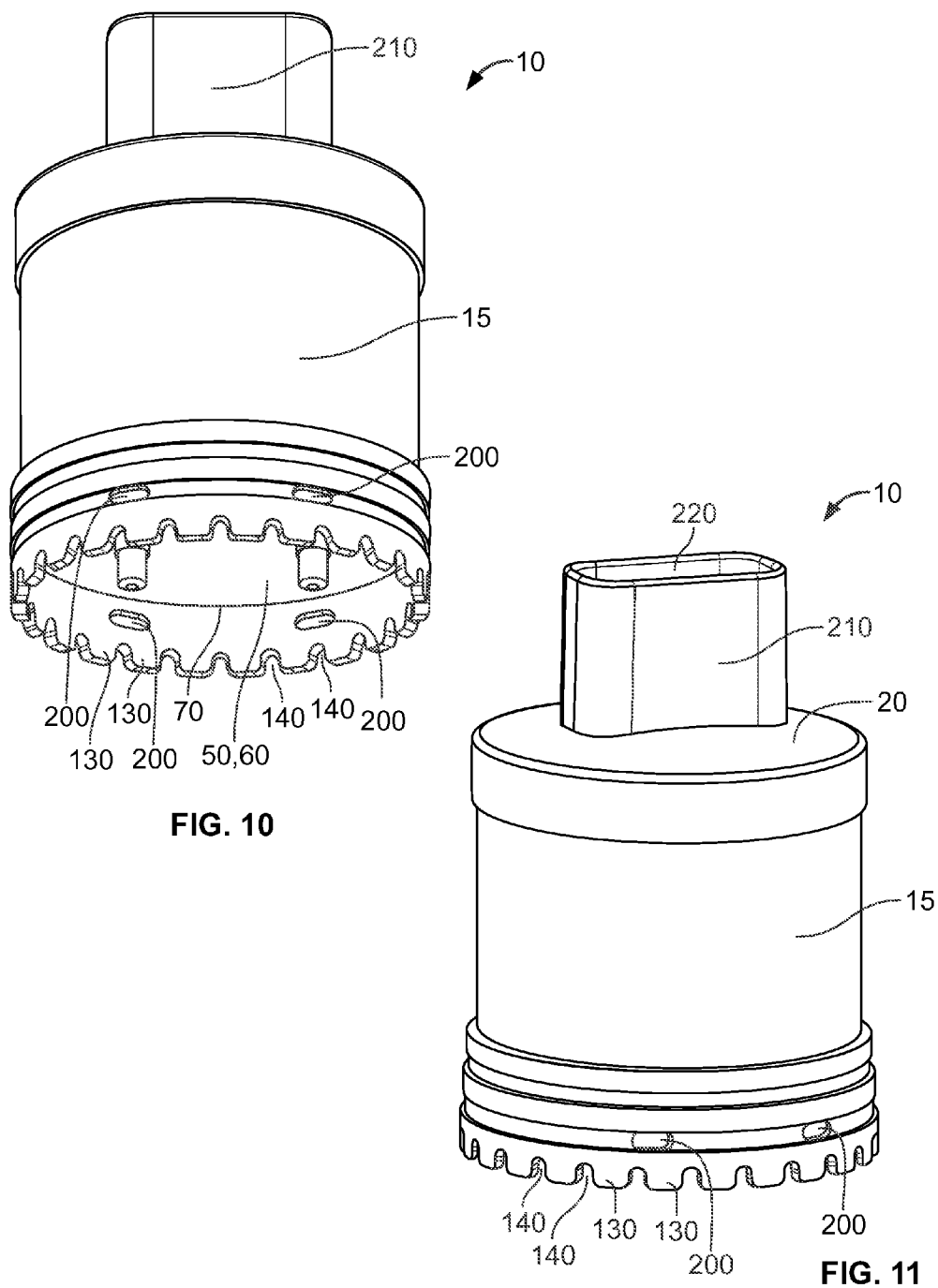

WATER LEAK WARNING DEVICE

CLAIM OF PRIORITY

This application is a continuation-in-part application claiming priority to U.S. application Ser. No. 13/837,759 filed on Mar. 15, 2013 which is a continuation-in-part U.S. application Ser. No. 13/477,183 filed on May 22, 2012 which claims priority to U.S. Provisional Patent Application 61/488,914, filed on May 23, 2011, the contents of all of which are fully incorporated herein by reference in their entirety.

FIELD OF THE INVENTION

The invention is directed at detecting water leak and signaling a warning. More particularly, this invention provides an easy-to-use, installation-free system to detect water leak and trigger an audible alarm.

BACKGROUND OF THE INVENTION

Many household devices use, store, and transport water in everyday life. A few examples of such devices include washing machines, water heaters, dish washers, toilets, fish tanks, flower beds, and sinks. These devices significantly improve the quality of life for millions of people. However, when not functioning properly or being handled erroneously, these devices may leak water that can cause sanitation hazards, health risks, and structural damages. In addition, some spots, such as basements and bathrooms, are prone to have water leakage and flood problems. It would be convenient to have a device that detects the water at the potential leak or flood spots and provides warnings regarding the leakage.

The current invention relates to a water leak warning device that provides immediate audible warnings when a water leak is detected. The utility of the invention is primarily to enable people to become aware of a water leakage close to a water-using device or a flood spot. In such a manner, whoever receives the warning will be able to act promptly to prevent further leakage and mitigate the damages.

Some previous inventions have tried to address the problem of water leakage and minor flooding. These devices are usually expensive and/or hard to use. The current invention enjoys a succinct yet elegant design that makes the device inexpensive, affordable, and maintenance-free. Moreover, the current invention is sturdy, easy to use, and does not require any installation. The user can simply put the device embodying the current invention at the spot that is flood-prone or likely to have a water leak. The device will deliver a warning when water leak or flooding does take place.

DESCRIPTION OF THE RELATED ART

U.S. Pat. No. 4,888,455 discloses a water leak detector and method thereof. The water leak detector has a pair of electrical contacts separated by a material that becomes frangible when moistened. When the separating material becomes moist, it breaks and the electrical contacts close, triggering an alarm.

U.S. Pat. No. 6,873,263 discloses a battery powered water leak detector and audible alarm held on a credit card sized plastic board that has sufficient unobstructed area for visible messages, such as advertising, to be printed of otherwise affixed thereon.

Various implements are known in the art, but fail to specifically and adequately address all the problems solved by the invention described herein. Two embodiments of this invention are illustrated in the accompanying drawings and will be described in more detail herein below.

SUMMARY OF THE INVENTION

A water leak warning device is described and taught having a hollow body having an interior space and an outer surface, the hollow body having walls comprising a bottom wall and a side wall, the bottom wall having a bottom flat surface; at least two electrodes each extending out of the bottom flat surface in a direction generally perpendicular to the bottom flat surface; a power supply enclosed in the interior space of the hollow body; and a speaker enclosed in the interior space of the hollow body; wherein the at least two electrodes, the power supply, and the speaker are operatively connected by conducting elements such that when the at least two electrodes are connected by a conductive material, an audible signal is emitted by the speaker.

The water leak warning device may also have a plurality of protruding elements having substantially equal height, being rooted on the lower end of the side wall and extending from the side wall in a direction generally perpendicular to the bottom flat surface, with gaps between the protruding elements. The protruding elements may also be rooted directly from the bottom surface. Such designs may allow any water that leaks onto the ground to flow through the gaps between the protruding elements and reach under the bottom flat surface of the water leak warning device.

The water leak warning device may further have two or more electrodes each having a first end and a second end, the first ends of the electrodes protruding out of the flat surface of the hollow body in a direction generally perpendicular to the flat surface, the length of the first ends extending out of the hollow body may be shorter than, equal to, or slightly longer than, the length of the protruding elements extending out of the peripheral edge of the bottom flat surface, the second ends of the electrodes being enclosed in the interior space of the hollow body. When the user puts the water leak warning device on the ground, the first ends of the electrodes may or may not have constant contact with the ground because the part of the electrodes extending out of the bottom flat surface may be slightly longer than, equal to, or shorter than, the length of the protruding elements extending out of the peripheral edge of the bottom flat surface. The gaps between the protruding elements ensure that leaked water can flow through to make contact with the first ends of the electrodes.

The water leak warning device further has a power supply, a speaker, and an amplifier, all of which are enclosed in the interior space of the hollow body. The electrodes, the power supply, the speaker and the amplifier are operatively connected by conducting elements such that when the first ends of the electrodes are connected by conductive material, such as water, an audible signal is emitted by the speaker. When leaked water reaches the spot where the warning device is placed, the first ends of the electrodes are connected through the water, thereby triggering an alarm. The user of the device can thus be warned and take actions to prevent further leakage and mitigate any damage.

In another embodiment there is a water leak warning device having a rectangular hollow body having an interior space, the hollow body having rigid walls comprising at least a top wall, a bottom wall, and a plurality of side walls, wherein there is an adhesive disposed on at least one of the plurality of side walls; at least two electrodes each having a first end extending out of the bottom wall in a direction generally perpendicular to the bottom wall; a power supply enclosed in the interior space of the hollow body; a speaker enclosed in the interior space of the hollow body; an aperture traversing at least one of the plurality of the side walls, wherein the at least two electrodes, the power supply, and the speaker are operatively connected by conducting elements such that when the first end of each of the at least two electrodes are connected by a conductive material, an audible signal is emitted by the speaker through the aperture traversing the at least one side wall; and a reverberating chamber partially or wholly surrounding the aperture.

It is an object of the present invention to provide a water leak warning device that is easy to use and does not require activation.

It is another object of the present invention to provide a water leak warning device that does not require installation and maintenance.

Yet another object of the present invention is to provide a water leak warning device that makes an audible alarm after the device is triggered.

Yet another object of the present invention is to provide a water leak device that may be triggered by different depths of water under the water leak warning device.

Still another object of the present invention is provide a water leak warning device that may be triggered immediately after water reaches the bottom of the water leak warning device.

Yet another object of the present invention is provide a water leak warning device that may be triggered after some water has accumulated under the water leak warning device.

Still another object of the present invention is to provide a water leak warning device that is sturdy and resistant to damages.

Yet another object of the present invention is to provide a water leak warning device that is inexpensive, disposable, and does not require battery changes.

Still another object of the present invention is to provide a water leak warning device that is small in scale and may be easily placed at any location.

BRIEF DESCRIPTION OF THE DRAWINGS

FIG. 10 is a bottom perspective view of a second preferred embodiment of a water leak warning device.

FIG. 11 is a top perspective view of a second preferred embodiment of a water leak warning device.

DESCRIPTION OF THE EMBODIMENTS

Figure 1:
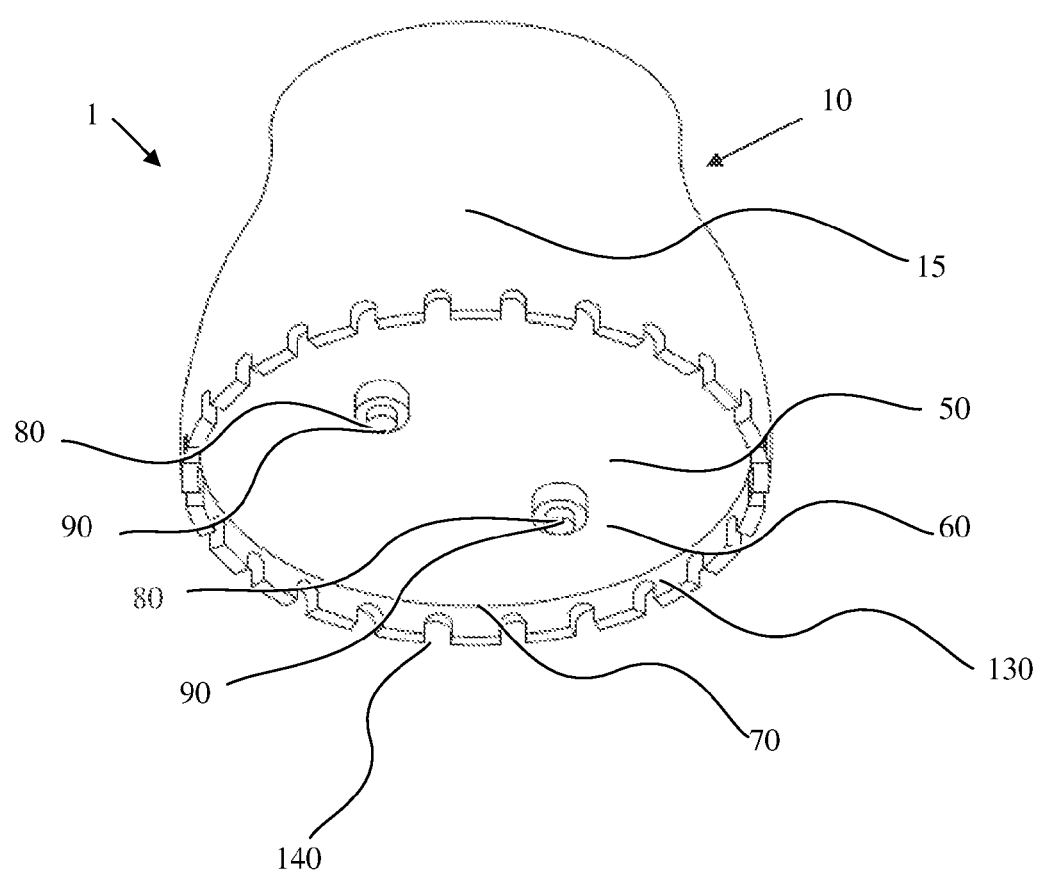
FIG. 1 is a bottom perspective view of the first preferred embodiment of a water leak warning device.

Where possible, identical elements in the various figures are identified with the same reference numerals. Reference will be made in detail to the two embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a bottom perspective view of a water leak warning device 1. Shown are a hollow body 10 having side wall 15 and bottom wall 50, the bottom wall 50 having a bottom flat surface 60, bottom peripheral edge 70, a plurality of protruding elements 130 having substantially equal height disposed on a lower end of the side wall 15 as extensions of the side wall 15 in a direction generally perpendicular to the bottom flat surface 60, wherein there are gaps 140 between the protruding elements 130; and electrodes 80 extending through the bottom wall 50, and the first ends 90 of the electrodes 80 protruding out of the bottom flat surface 60 in a direction generally perpendicular to the bottom flat surface 60.

Figure 2:
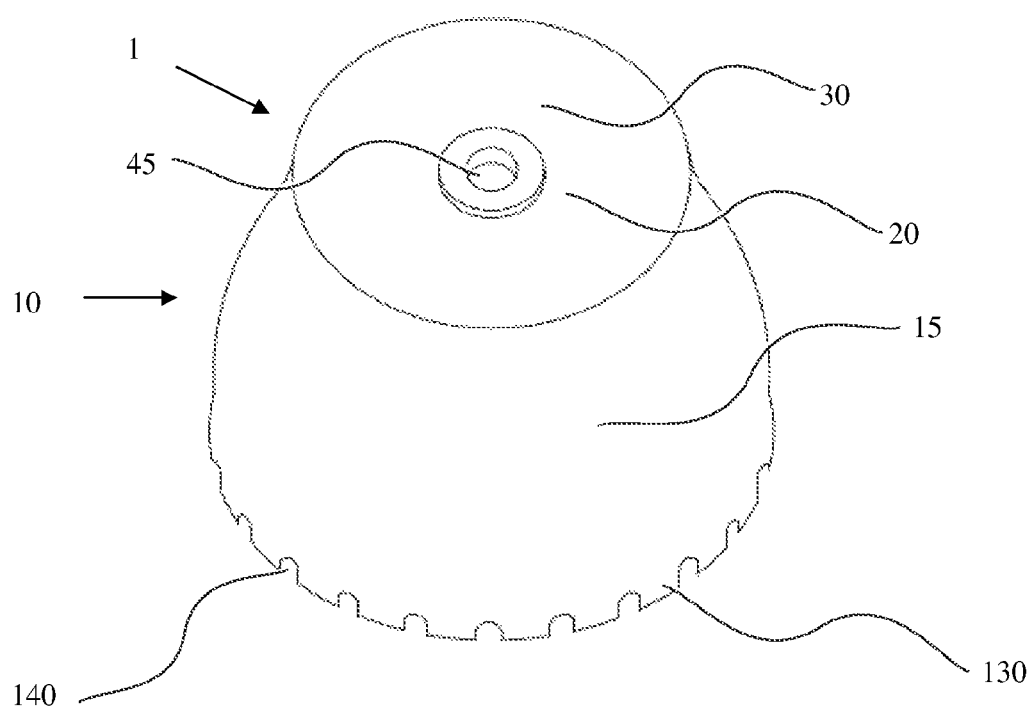
FIG. 2 is a top perspective view of the first preferred embodiment of a water leak warning device.

FIG. 2 shows a top perspective view of the first preferred embodiment of a water leak warning device 1. Shown are a hollow body 10 having side wall 15 and top wall 20 with a top surface 30, the protruding elements 130, the gaps 140, and an opening 45 on the top wall 20.

The hollow body 10 is preferably made out of a hard and non-conductive material, such as, but not limited to a plastic or a composite material. Other possible materials for the hollow body 10 may include polymers and resins including but not limited to plastic, rubber, foam, silicone, ABS, Polycarbonate, Noryl™, PVC, Polystryrene, ABS/PVC, PVC/Acrylic, Polysulfone, Acrylic, Polyethylene, and Kydex™. The rigid hollow body 10 is preferred to be able to sustain pressure such as the incidental stepping by the user of the water leak warning device 1. The hollow body 10 is pictured to have a substantially tapered column shape, but may be cubic, tetrahedral or any other shape that may represent functional or decorative purposes.

The first preferred size of the hollow body 10 is between one and two inches in height, between one and 1½ inches (2.5-3.8 cm) in top wall 20 diameter and between 1½ and two inches (3.8-5.1 cm) in bottom wall 50 diameter. The precise dimensions of an embodiment may be dictated by a potential or actual application. But the embodiment is preferred to be small so that the water leak warning device 1 can be place in clustered spots. If the embodiment is in a shape other than a tapered column, the overall width of the water leak warning device 1 is preferred to be less than two inches. The water leak warning device 1 may be placed on or near a potential water leak spot such as, but not limited to, to sinks, fish tanks, refrigerators, dish washers, water heaters and flower beds.

The first ends 90 of the electrodes 80 preferably extend outside the bottom wall 50 of the hollow body 10 for about two millimeters. The extension of the first ends 90 of the electrodes 80 out of the bottom flat surface 60, defined as a first height, should be close to the length that tip of the protruding elements 130 extending beyond the bottom surface 70, defined as a second height. Since the first height and the second height are close, the electrodes 80 do not bear most of the weight of the water leak warning device 1 even if the first height is larger or exactly the same as the second height. The protruding elements 130 provide most of the support for the water leak warning device 1. When the first height is larger or exactly the same as the second height, the first ends 90 of the electrodes 80 constantly touch the ground, ensuring triggering of the water leaking warning device even with minimum amount of water. When pressure is placed on the hollow body 10, the protruding elements 130 may prevent the first ends 90 of the electrodes 80 from being damaged by physical force. It is also possible that the first height is smaller than the second height. With such a design, the first ends 90 of the electrodes 80 do not touch the ground when the water leak warning device is placed on a flat surface. Thus, only some accumulation of water under the device would trigger the device. This design is suitable for locations that may susceptible to regular moisture but substantial accumulation of water may result in damages. The exact design as to the compared length of the first height and the second height may be determined according to the intended use of the water leak warning device.

The first embodiment shown in FIGS. 1-2 includes two electrodes. However, it should be noted that the number of electrodes may vary according to the specific design of the circuits. The number of electrodes in a single water leak warning device may be 2, 3, or 4, wherein a person skilled in the art may arrange the circuits so that the alarm may be triggered by connecting all the electrodes or by connecting any 2 of the electrodes.

The protruding elements 130 are preferably natural extensions of the side wall 15. However, the protruding elements 130 may also be rooted directly on the bottom wall 50. As long as the protruding elements 130 serve to elevate the hollow boy 10 from the floor, the positioning of the protruding elements 130 may vary. The protruding elements 130 may be any shape, but they preferably have about the same height. It is preferable that the protruding elements 130 be evenly distributed on the bottom peripheral edge 70. There should be gaps between the protruding elements 130 so that leaked water may flow pass the protruding elements 130 and reach the first ends 90 of the electrodes 80 under the bottom flat surface 60.

Figure 3:
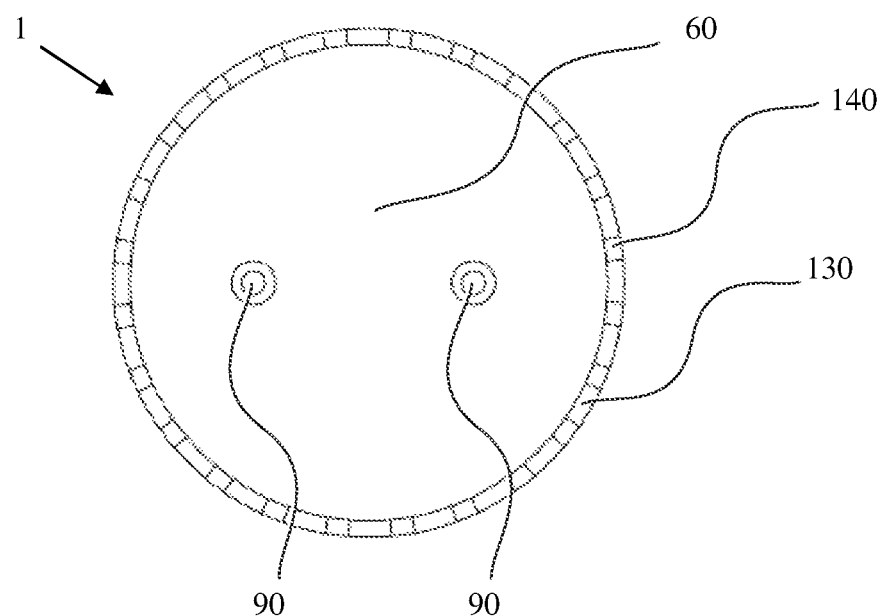
FIG. 3 is a bottom view of the first preferred embodiment of a water leak warning device.
Figure 4:
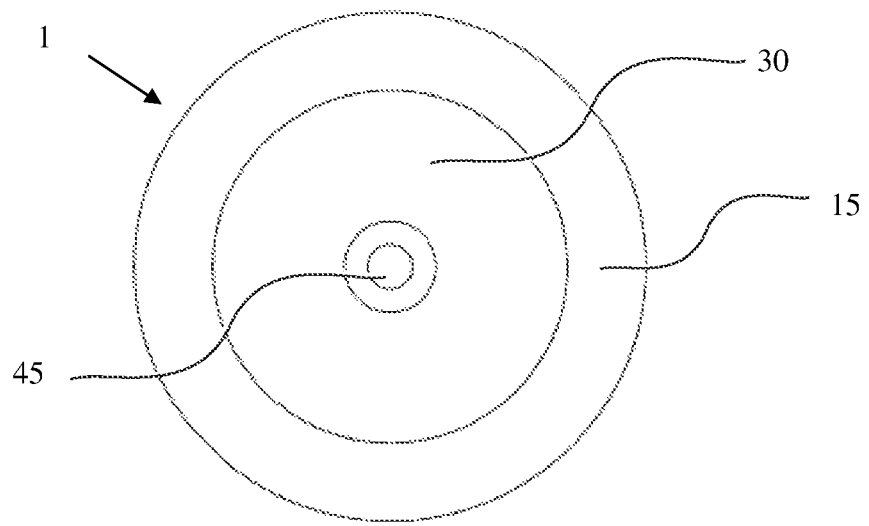
FIG. 4 is a top view of the first preferred embodiment of a water leak warning device.

FIG. 3 shows a bottom view of the water leak warning device 1. Shown are the bottom flat surface 60, the protruding elements 130, the gaps 140, and the first ends 90 of the electrodes 80. FIG. 4 shows a top view of the water leak warning device 1. Shown are the top wall 30, the side wall 15, and the opening 45 on the top wall 30.

Figure 5:
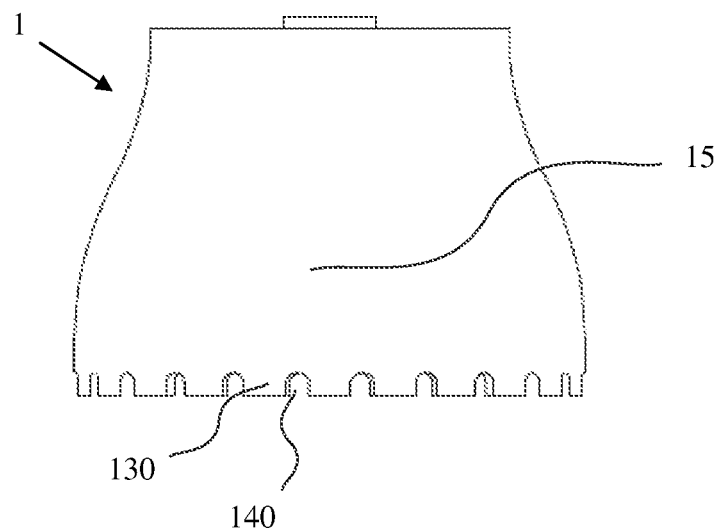
FIG. 5 is a front view of the first preferred embodiment of a water leak warning device.
Figure 6:
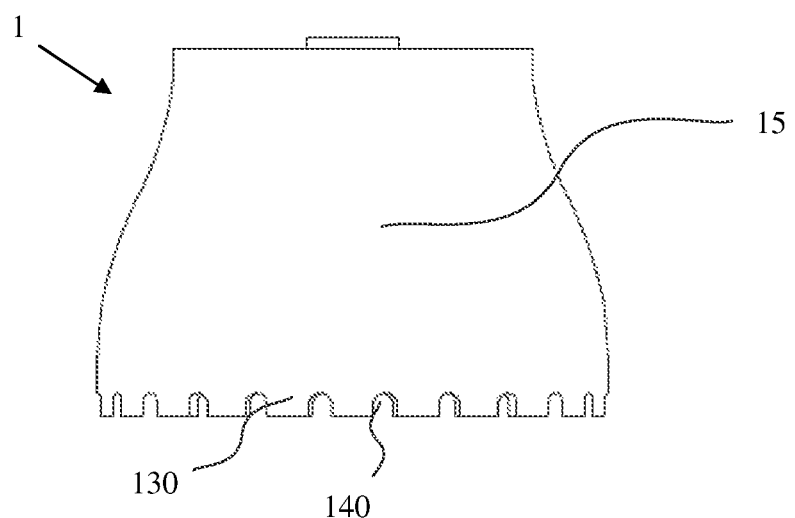
FIG. 6 is a side view of the first preferred embodiment of a water leak warning device.

FIG. 5 shows a front view of the water leak warning device 1. Shown are the side wall 15, the protruding elements 130, and the gaps 140. Since this preferred embodiment of the water leak warning device 1 has a tapered column shape with a round top wall 20 and round bottom wall 50, the rear view of the water leak warning device 1 is a minor image of FIG. 5. FIG. 6 shows a side view of the water leak warning device 1. Shown are the side wall 15, the protruding elements 130, and the gaps 140. Since this preferred embodiment of the water leak warning device 1 has a tapered column shape with a round top wall 20 and round bottom wall 50, the side view of the water leak warning device 1 is an exact replica of FIG. 5 and the view from the other side is a mirror image or FIG. 6.

Figure 7:
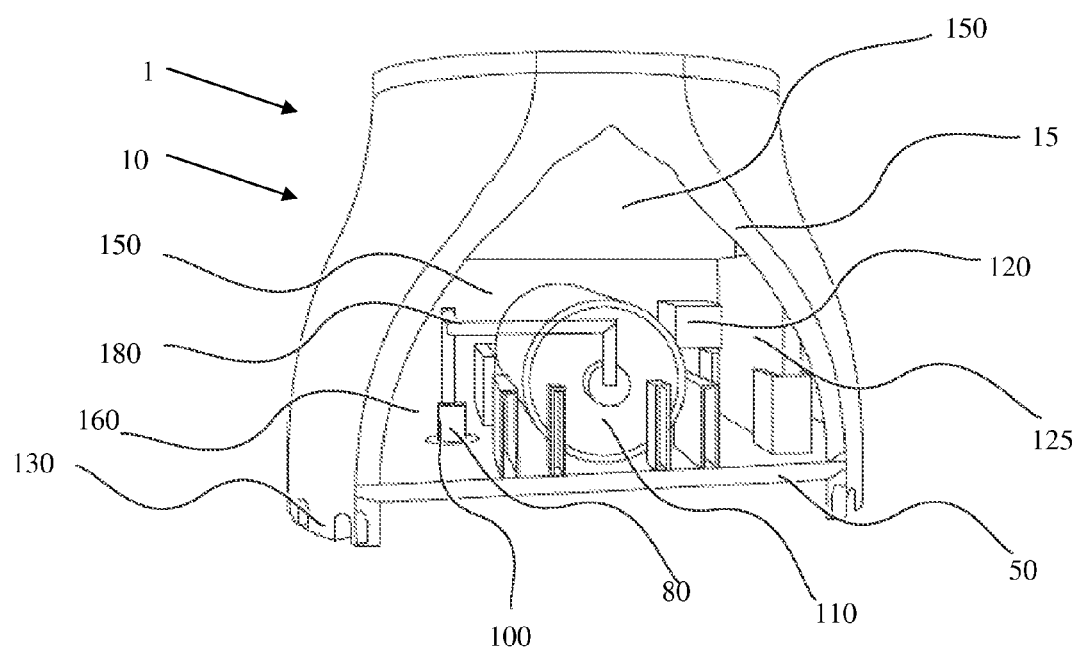
FIG. 7 is a perspective view of the shallow cross section of the first preferred embodiment of a water leak warning device.

FIG. 7 shows a perspective view of a shallow cross section of the water leak warning device 1. Shown are the hollow body 10, the side wall 15, the bottom wall 50, the protruding elements 130, a power supply 110, representative wires 180, a lower compartment 160, an upper compartment 150, the second ends 100 of the electrodes 80, an amplifier 120, and a circuit board 125.

The preferred power source 110 for the present invention is a battery producing 12 Volts. However, higher or lower battery power may be required depending on the size and expected duration of the water leak warning device 1. The power supply 110 may not be replaceable during the regular operation of the device. More particularly, the power supply 110 may be irreplaceably disposed in the water leak warning device 1, meaning that the power supply 110 cannot be replaced without damaging the physical integrity of the enclosing structures, such as the side, bottom, and/or top walls. The water leak warning device 1 may be designed to be disposable and that it should therefore be replaced after being in use for a certain period of time that may be indicated by the easily read indicium. It may also be recommended that the device be replaced after a water leak is detected.

The first preferred amplifier 120 for the present invention is a transistor amplifier. It may be a single transistor amplifier or it may be a more complex multiple transistor amplifier. In consideration of keeping the water leak warning device 1 more affordable, a single transistor amplifier is preferred. The amplifier 120 may, for instance, be lodged on a circuit board 125.

The interior space of the hollow body 10 may be roughly divided into an upper compartment 150 and a lower compartment 160. The division of the interior space of the hollow body 10 facilitates the arrangement of the elements for the water leak warning device 1. However, other designs for arranging the interior space are also possible as long as the elements can be effective connected.

Figure 8:
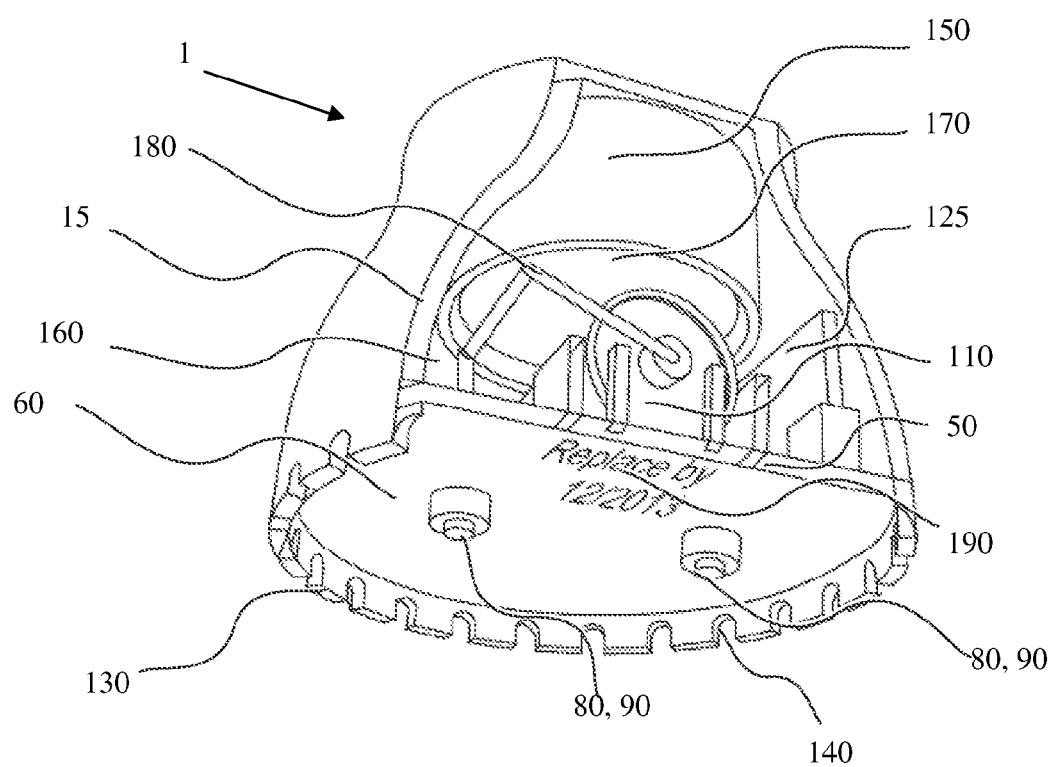
FIG. 8 is a bottom perspective view of the shallow cross section of the first preferred embodiment of a water leak warning device.

FIG. 8 shows a lower perspective view of a shallow cross section of the water leak warning device 1. Shown are the hollow body 10, the side wall 15, the bottom wall 50, the protruding elements 130, the gaps 140, the power supply 110, representative wires 180, the lower compartment 160, the upper compartment 150, the first ends 90 of the electrodes 80, the amplifier 120, the circuit board 125, a speaker 170, and an indicium 190 on the bottom flat surface 60 to indicate the time after which the device may no long function effectively.

The interior space of the hollow body 10 may be roughly divided into an upper compartment 150 and lower compartment 160. The power supply 110, the second ends 100 of the electrodes 80, the amplifier 120, and the circuit board may be enclosed in the lower compartment 160. The speaker 170 may be enclosed in the upper compartment 150. Overall, the hollow body 10 may enclose all the essential elements of the water leak warning device 1. In such a manner, the sturdy walls of the hollow body 10 provide protection to the circuit and prevent damages that may affect the function of the device.

The electrodes 80, the power supply 110, the amplifier 120, and the speaker 170 may be operatively connected by conductive elements such as wires 180. The wires 180 that are shown in FIGS. 7 and 8 are only representative. A person skilled in the art should be able to connect the electrodes 80, the power supply 110, the amplifier 120, and the speaker 170 to ensure that: when the first ends 90 of the electrodes 80 are connected by conductive material, the circuit closes and the speaker may emit an audible signal. In addition, a light, such as a small LED bulb, may be added to the circuit to enhance the signaling of the device. After the water leak warning device 1 is placed at a potential leak or flooding spot, leaked water may flow through the gaps 140 between the protruding elements 130 and reach the first ends 90 of the electrodes 80, thus triggering an audible alarm and possibly a light and providing a warning to the user of the water leak warning device 1 to take actions to prevent further leakage and mitigate damages.

The speaker 170 can be any type of device capable of producing an audible signal. To make the speaker fit into the hollow body 10, the speaker is preferably small in size. The speaker is preferred to be less that one inch for its longest dimension. The speaker may be an electronic magnetic buzzer or a piezoelectric ceramic buzzer that is capable of emitting audible sound to warn the user of the water leak warning device 1.

FIG. 8 also shows an optional easily read indicium 190 on the bottom flat surface 60 of the hollow body 10. The optional indicium 190 serves to indicate a time after which the device may no longer function effectively. The easily read indicium 190 may, for instance, be an alphanumeric marking such as, but not limited to, a recommended replacement date, a date after which the device's battery may no longer be operative, or date after which the manufacturer is no longer willing to guarantee functioning, or some combination thereof. The indicium 190 may be marked on the bottom flat surface 60. But it can also be marked on other exterior surfaces of the hollow body 10 as long as the indicium 190 is clearly visible.

Figure 9:
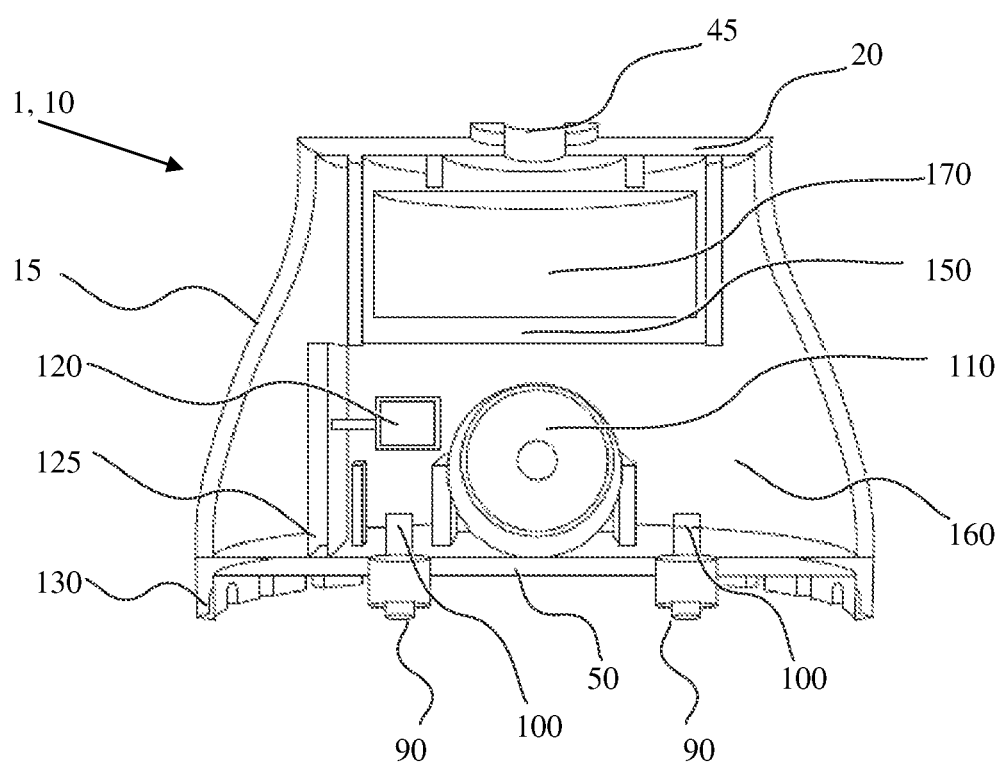
FIG. 9 is a side view of the cross section across the middle of the first preferred embodiment of a water leak warning device.

FIG. 9 shows a side view of a cross section across the middle of the hollow body 10 of the water leak warning device 1. Shown are the hollow body 10, the side wall 15, the protruding elements 130, the power supply 110, the lower compartment 160, the upper compartment 150, the first ends 90 and second ends 100 of the electrodes 80, the amplifier 120, the circuit board 125, the speaker 170, and an opening 45 on the top wall 20.

The opening 45 on the top wall 20 may be adjacent to the upper compartment 150, which houses the speaker 170. The opening 45 allows effective spreading of the signal emitted by the speaker 170 once the water leak warning device 1 is triggered. The opening is preferred to be not too small to prevent the emission of sound. However, the opening is preferred to be not too big to allow high possibility of contamination by water or other liquid. In the first preferred embodiment, the opening may be between 1/16 to 1/4 inches.

FIGS. 10-16 as a group show the details of a second preferred embodiment of the current invention. This embodiment shares most of the features of the embodiments described above, with the key difference being the addition of a reverberating chamber and a plurality of releasing orifices. It should be noted that not all the limitations for the first preferred embodiment will be recited in describing FIGS. 10-16. The designs included in the description of the first preferred embodiment, especially the ones related to the internal structures of the first preferred embodiment, are deemed included as long as such designs do not conflict with the additional features.

FIG. 10 is a bottom perspective view of a second preferred embodiment of a water leak warning device. Shown are a hollow body 10 having side wall 15 and bottom wall 50, the bottom wall 50 having a bottom flat surface 60, bottom peripheral edge 70, a plurality of protruding elements 130 having substantially equal height rooted on a lower end of the side wall 15 as extensions of the side wall 15 in a direction generally perpendicular to the bottom flat surface 60, wherein there are gaps 140 between the protruding elements 130; and electrodes 80 extending through the bottom wall 50, and the first ends 90 of the electrodes 80 protruding out of the bottom flat surface 60 in a direction generally perpendicular to the bottom flat surface 60. A reverberating chamber 210 is disposed on top of the hollow body 10. There are releasing orifices 200 through the side wall 15 beneath the bottom flat surface 60. For clarity purposes, not all the protruding elements 130 and gaps 140 are marked.

FIG. 11 is a top perspective view of a second preferred embodiment of a water leak warning device. Shown are a hollow body 10 having side wall 15 and top wall 20, the protruding elements 130 and the gaps 140. A reverberating chamber 210 is disposed on top of the hollow body 10, the reverberating chamber encircles a top opening 45 (not shown in FIG. 10) on the top wall 30 and having a sound outlet 220. There are releasing orifices 200 through the side wall 15 beneath the bottom flat surface 60.

The reverberating chamber 210 is designed to enhance the audio signals coming out of the top opening 45. The reverberating chamber 210 may be any shape encircling the top opening 45 and having a sound outlet 220, preferably on top. Field tests confirm the effectiveness of the reverberating chamber 210, which increases the decibel level of the sound output.

Just like the first preferred embodiments, the extension of the first ends 90 of the electrodes 80 out of the bottom flat surface 60, defined as a first height, may be shorter than, equal to, or longer than the length that tip of the protruding elements 130 extending beyond the bottom surface 70, defined as a second height. The first height may have a range of 1/32 to 1 inch (0.8 to 25.4 mm); the second height may have a range of 1/32 to 1 inch (0.8 to 25.4 mm).

When the first height is shorter than the second height, the first ends 90 of the electrodes 80 do not touch the ground when the water leak warning device is placed on a flat surface. Thus, only with some accumulation of water under the device, would the device be triggered. This design is suitable for locations that may susceptible to regular moisture but substantial accumulation of water may result in damages. For example, water leak warning device having such a design may be put in water heater pans or HVAC condensing pans. Two preferred models of the water leak warning device have a first height 1/8 inch or 1/16 inch shorter than the second height, respectively.

On the other hand, the first height may be the same as or minimally longer than the second height. Such a design allows the electrodes to touch the ground when the water leak warning device is placed on a flat surface. With such a design, the water leak warning device is triggered with minimal amount of moisture. For example, water leak warning device having this design may be paced close to water heaters, sinks, sump pumps, washing machines, hydronic heating apparatus, toilets, and other structures that need immediate warning for water leak.

The releasing orifices are designed to deal with another problem. Excessive accumulation of water may result in air being sealed under the bottom wall 50 and even the tipping over of the water leak warning device 1. In that case, even if the warning sound is properly triggered, it may stop if the water leak warning device is toppled. The releasing orifices 200 are designed to solve this problem. When water flows through the gaps 140 under the water leak warning device 1, air under the bottom surface 60 may be compelled away through the releasing orifices 200, preventing the toppling of the water leak warning device 1.

Figure 12:
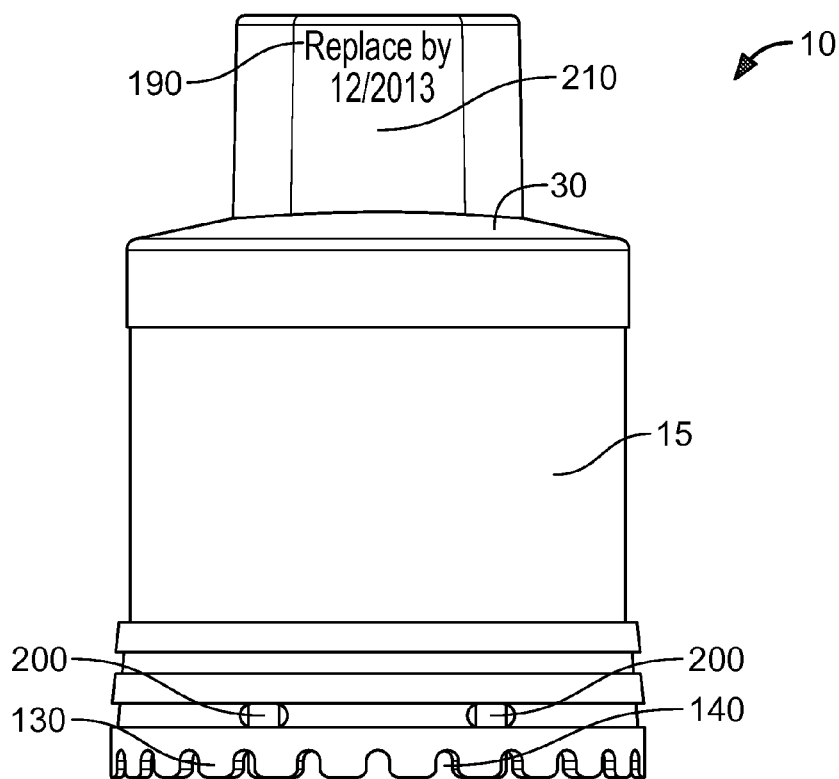
FIG. 12 is a front view of the second preferred embodiment of a water leak warning device.

FIG. 12 is a front view of the second preferred embodiment of a water leak warning device. Shown in FIG. 12 is the hollow body 10 having a side wall 15, a top wall 30, the protruding elements 130, the gaps 140, and releasing orifices 200. There is a reverberating chamber 210 on the top of the hollow body 10. The front blank space of the side wall may be used to receive inscriptions such as a logo or a trademark. An indicium 190 shows a potential expiration date of the device.

Figure 13:
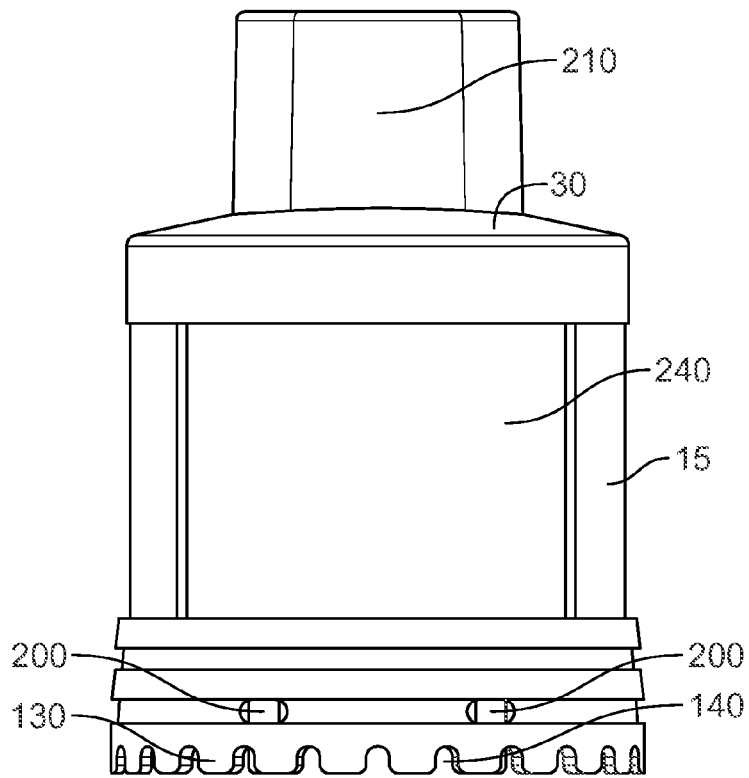
FIG. 13 is a back view of the second preferred embodiment of a water leak warning device.

FIG. 13 is a back view of the second preferred embodiment of a water leak warning device. Shown in FIG. 13 is the hollow body 10 having a side wall 15, a top wall 30, the protruding elements 130, the gaps 140, and releasing orifices 200. There is a reverberating chamber 210 on the top of the hollow body 10. In addition, shallow ridges on the side wall 15 make up a label area 240. The label area is preferred to have a 1×1.5 inch (2.5×3.8 cm) size. The label area may be used to receive labels that may serve as mini-advertisements for plumbers or other merchants.

Figure 14:
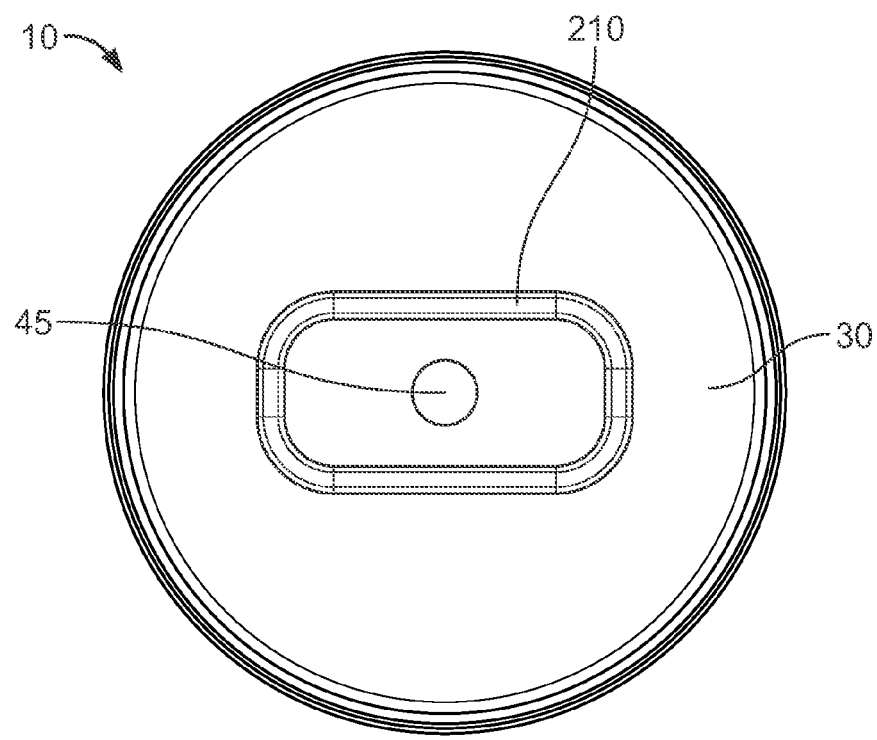
FIG. 14 is a top view of the second preferred embodiment of a water leak warning device.

FIG. 14 is a top view of the second preferred embodiment of a water leak warning device. Shown in FIG. 14 is the hollow body 10 having a top wall 30 and top opening 45 on the top wall 30. There is a reverberating chamber 210 on the top of the hollow body 10 encircling the top opening 45.

Figure 15:
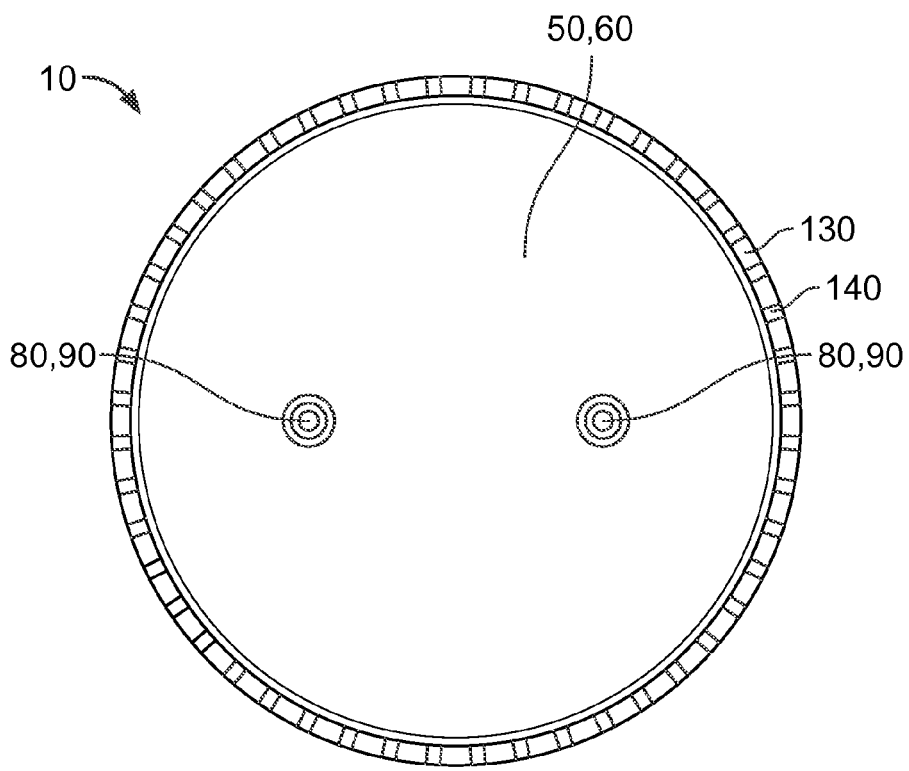
FIG. 15 is a bottom view of the second preferred embodiment of a water leak warning device.

FIG. 15 is a bottom view of the second preferred embodiment of a water leak warning device. Shown in FIG. 15 is the hollow body 10 having a bottom wall 50 with a bottom flat surface 60, the protruding elements 130, the gaps 140, and the first ends 90 of the electrodes 80.

Figure 16:
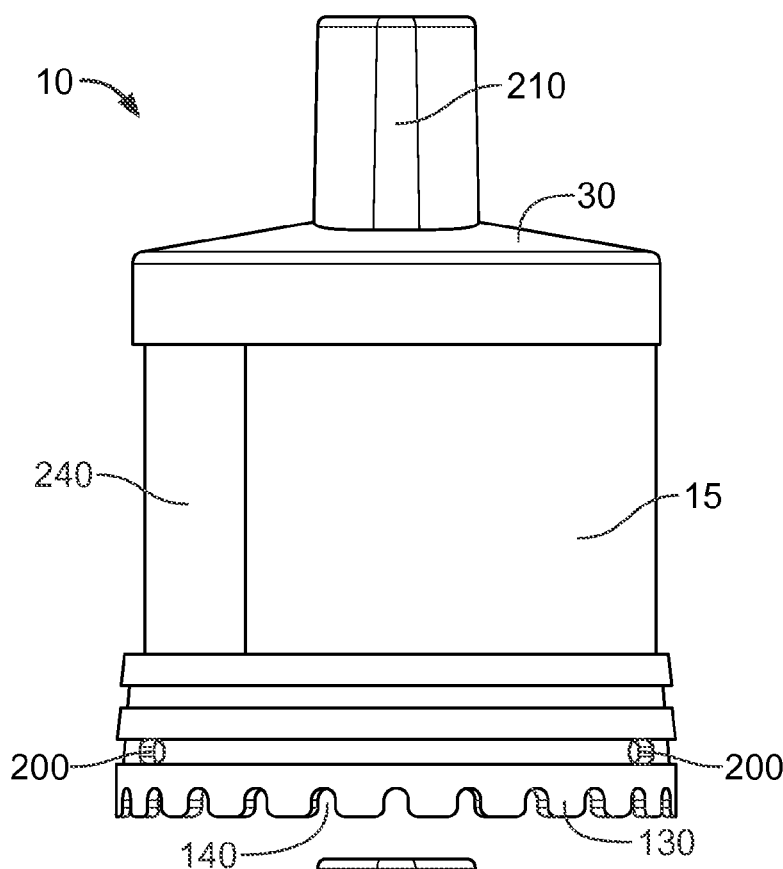
FIG. 16 is a first side view of the second preferred embodiment of a water leak warning device.

FIG. 16 is a first side view of the second preferred embodiment of a water leak warning device. Shown in FIG. 16 is the hollow body 10 having a side wall 15, a top wall 30, the protruding elements 130, the gaps 140, the reverberating chamber 210 on the top of the hollow body 10, the label area 240, and releasing orifices 200.

Figure 17:
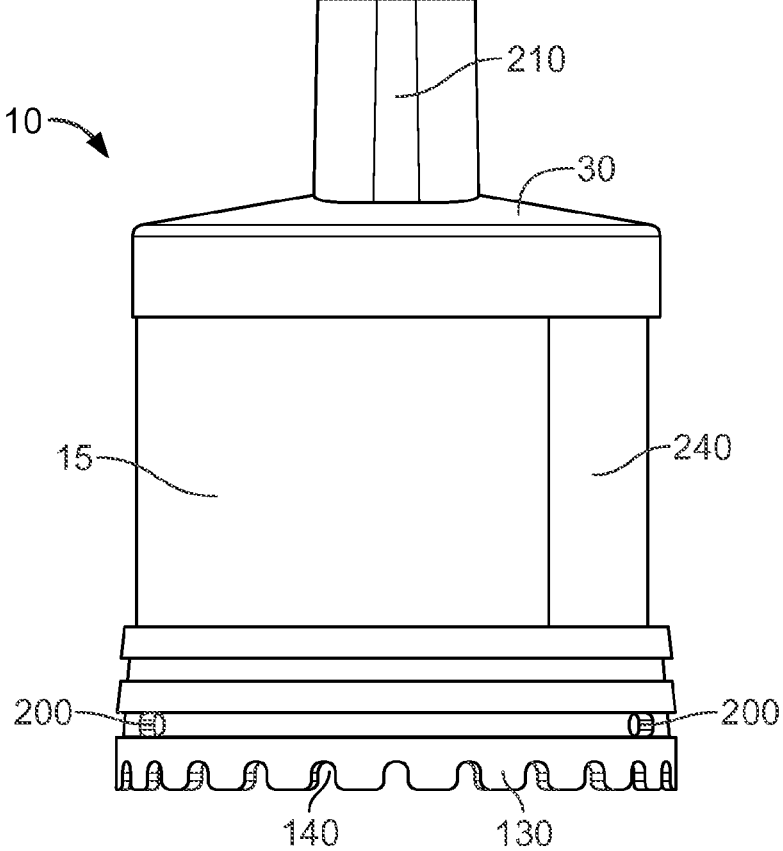
FIG. 17 is a second side view of the second preferred embodiment of a water leak warning device.

FIG. 17 is a second side view of the second preferred embodiment of a water leak warning device. Shown in FIG. 16 is the hollow body 10 having a side wall 15, a top wall 30, the protruding elements 130, the gaps 140, the reverberating chamber 210 on the top of the hollow body 10, the label area 240, and releasing orifices 200.

Figure 18:
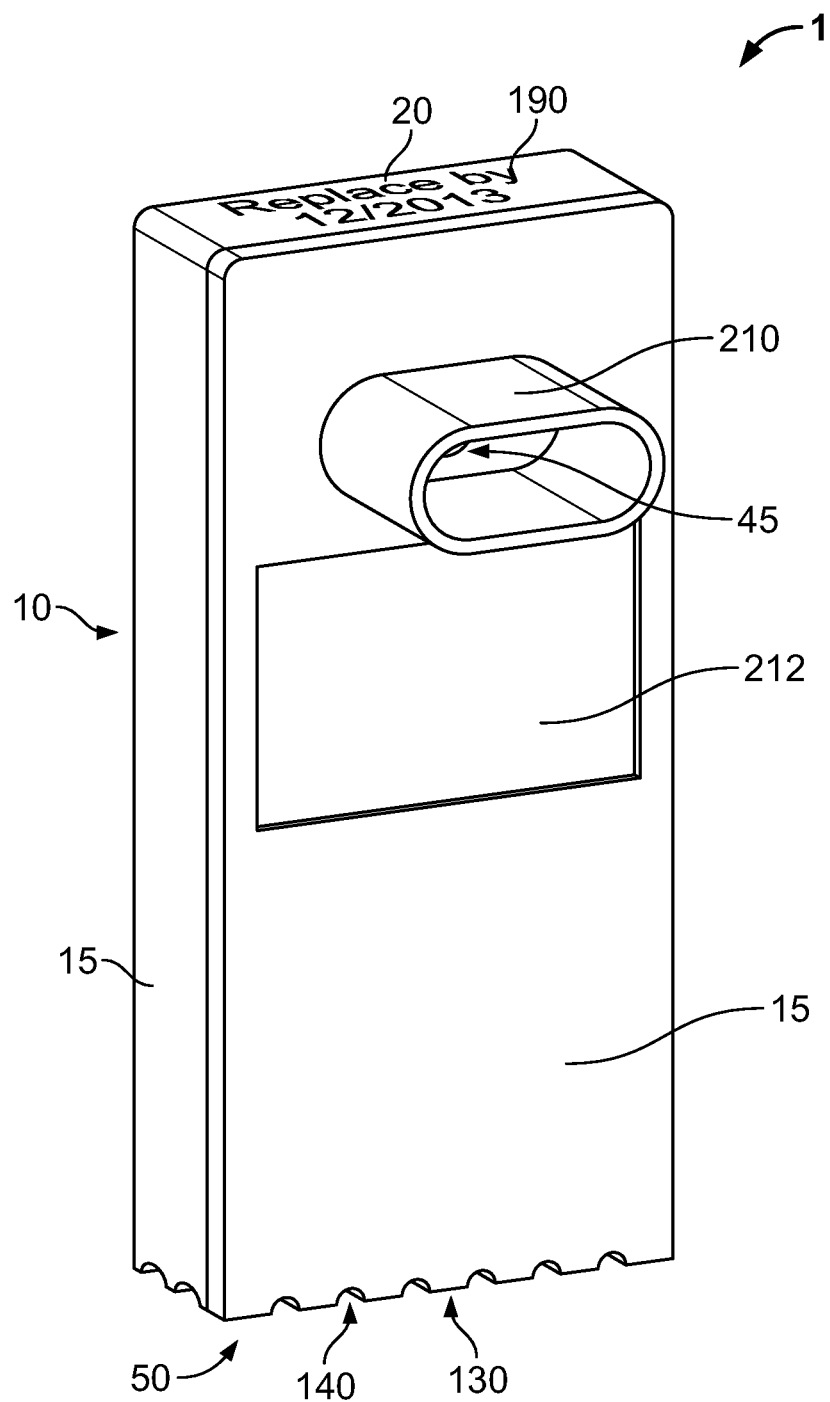
FIG. 18 is a perspective view of a third preferred embodiment of a water leak warning device.

Referring now to FIG. 18, there is a third embodiment of the present invention. Here, the water leak warning device 1 has a substantially rectangular hollow body 10. The hollow body 10 generally comprises a top wall 20, bottom wall 50, and a plurality of sidewalls 15. On one of the plurality of sidewalls 15 there may be an indentation 212. This indentation 212 is sized for a label or other advertisement (inlay) to be permanently or removably positioned. The indentation 212 should allow for the label or the like to be adhered and held flush to the sidewall surface. Along the top wall 20 there is an indicium 190 which, in this case, is an expiration date. This is the date after which the device may no longer function correctly and may need to be replaced or have some component of the device replaced.

Additionally, on one of the plurality of sidewalls 15 there is an opening 45. This opening 45 provides an avenue for the sound emitted by the speaker 170 (see FIG. 8) to emanate from the hollow body 10. The opening 45 is surrounded by a reverberating chamber 210 extending perpendicularly from one of the plurality of sidewalls 15. The reverberating chamber 210 is designed to enhance the audio signals coming out of the opening 45. As such, the reverberating chamber 210 may be any shape and may surround the opening wholly or in part.

The bottom edge of the plurality of sidewalls 15 has a number of gaps 130 and protruding elements 140. The protruding elements 140 allow the water leak warning device 1 to sit substantially flat in relation to the surface on which it is resting. The gaps 130 provide a channel for water or another liquid to pass through and contact the electrode(s) 80 (see FIG. 19). The gaps 130 and protruding elements 140 are present around the entire periphery of the hollow body 10 along the bottom edge of the plurality of sidewalls 15.

Figure 19:
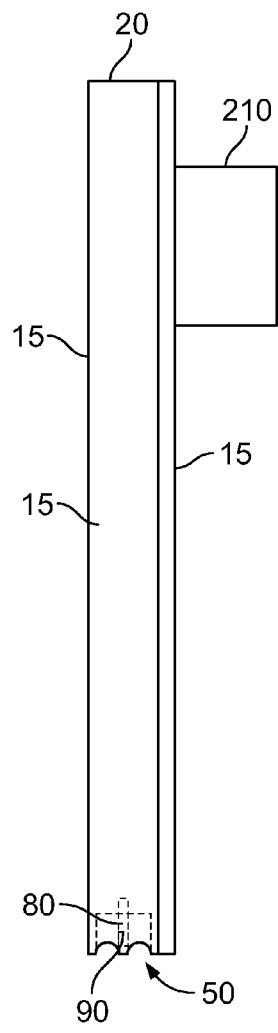
FIG. 19 is a side view of a third preferred embodiment of a water leak warning device.

Referring now to FIG. 19, there is a side view of the embodiment shown in FIG. 18. Each of the plurality of sidewalls 15, the top wall 20, and bottom wall 50 are shown. The reverberating chamber 210 is shown protruding from one of the plurality of sidewalls 15. The size of the reverberating chamber 210 may vary and the distance of protrusion may vary as well. Different sounds may be created by shaping and changing the dimensions of the reverberating chamber 210.

Protruding from the bottom wall 50, there is an electrode 80 with a first end 90. The electrode 80 functions as described above and preferably in tandem with a second electrode (see FIG. 8). When the first end 90 of each of the electrodes 80 contacts a liquid, the circuit is completed, and the speaker produces a sound which alerts an individual to the presence of the liquid, leak, flood, or the like.

Figure 20:
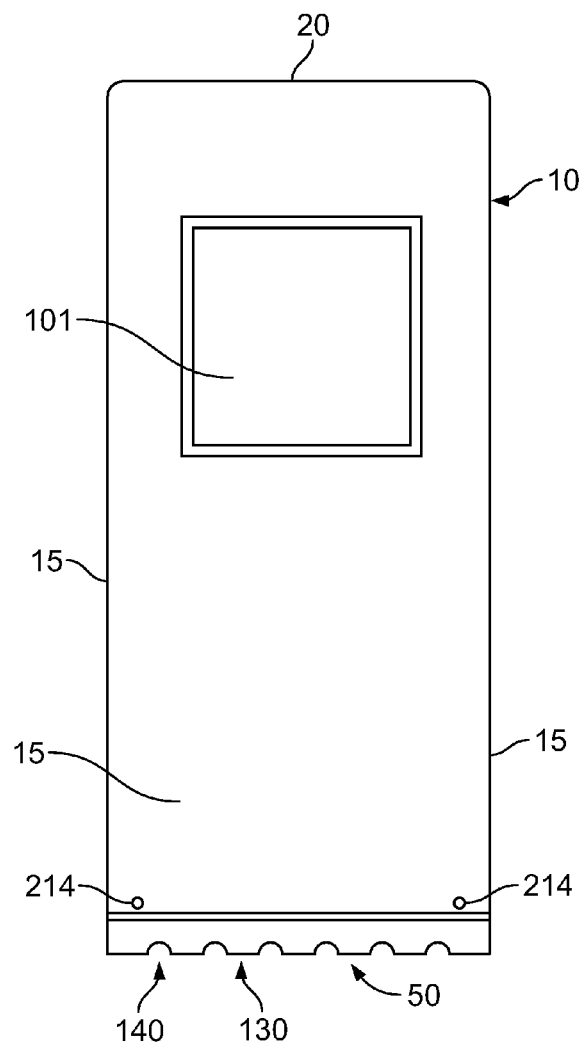
FIG. 20 is a back view of a third preferred embodiment of a water leak warning device.

In FIG. 20, there is a back view of the water leak warning device 1. The hollow body 10 has a top wall 20, bottom wall 50, and a plurality of sidewalls 15. On one of the plurality of sidewalls 15 there is an adhesive 101 disposed thereon. The adhesive 101 may be any type of adhesive substance such as but not limited to tapes, glues, epoxies, and the like or any combination thereof. The adhesive 101 may be permanent or removable. Preferably, the adhesive 101 is a double sided tape.

The adhesive 101 allows the water leak warning device 1 to be abutted against a secondary object such as a hot water heater. The presence of the adhesive 101 helps to ensure the water leak warning device 1 is not knocked over inadvertently or by a torrent of liquid. Further, there is at least one air release hole 214 which helps to facilitate the flow of air under and through the water leak warning device 1. These air release holes 214 may be present in any number along any of the plurality of sidewalls 15 of the present invention.

Figure 21:
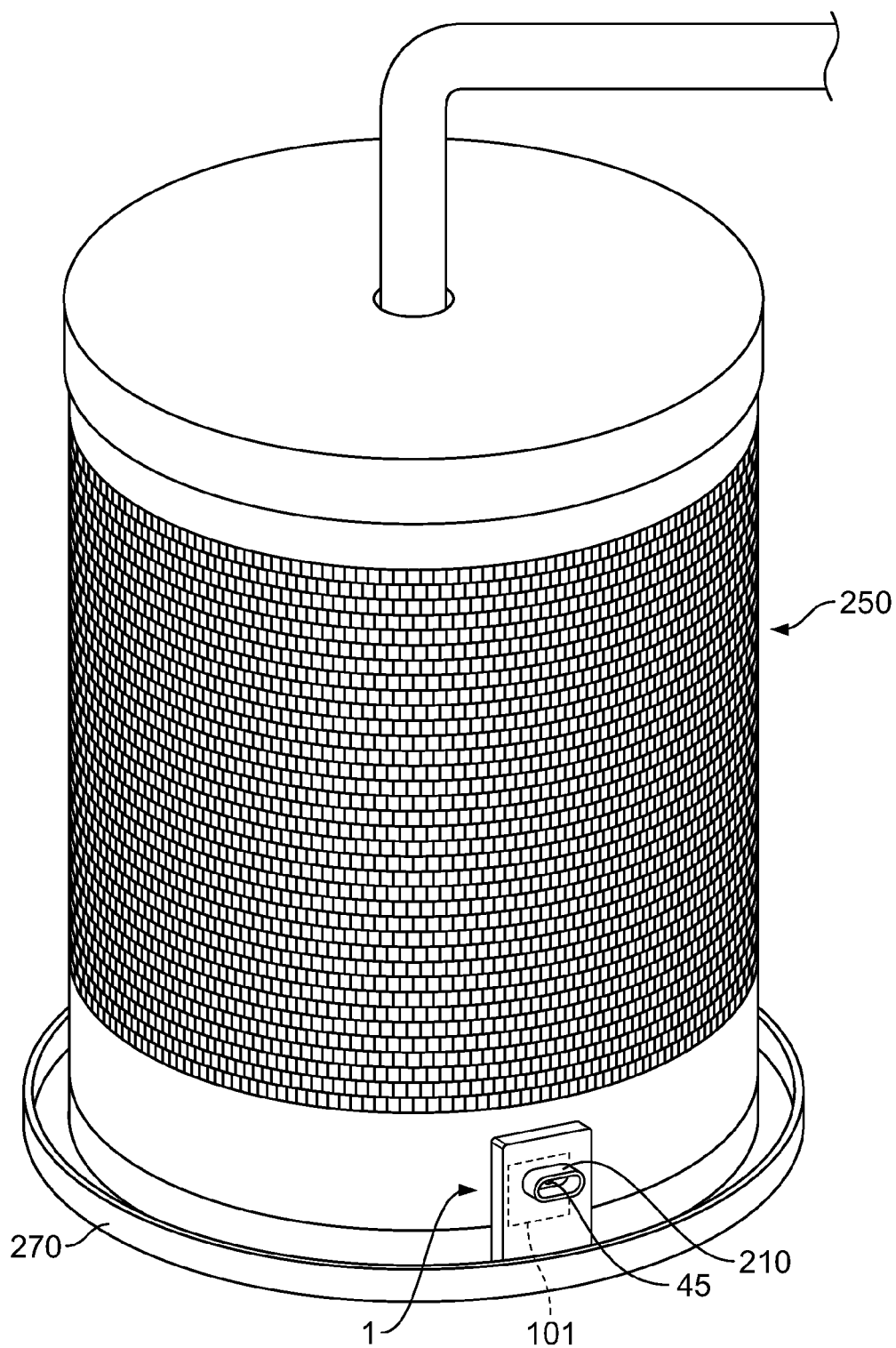
FIG. 21 is a perspective view of a third preferred embodiment in one intended usage.

Referring now to FIG. 21, the water leak warning device 1 is shown in one potential usage. The water leak warning device 1 has been positioned in a pan 270 with a water heater 250 also positioned therein. The water leak warning device 1 is sized to fit alongside the water heater 250 without obstructing the function of the water leak warning device 1. The water leak warning device 1 is further sized to fit between the hot water heater or similar device and the pan 270. As such, the thickness of the water leak warning device 1 may vary while the preferred ratio of about 2:1 of the length and width remain the same. In some cases, the length, width, and thickness can all independently vary based on the required needs and spatial arrangements. The adhesive 101 ensures the water leak warning device 1 is coupled to the outer surface of the water heater 250 to prevent the device from being knocked over or otherwise inadvertently positioned incorrectly.

In addition, the adhesive 101 provides securement when the pan 270 is not present for added support. Thus, this provides the flexibility for the water leak detection device 1 to easily and effectively be used with any number of objects having a surface to which the device can be coupled. When water leaks into the pan 270 and makes contact with the electrodes 80 (see FIG. 19) the speaker generates an alarm which is emanated through the opening 45 and is amplified by the reverberating chamber 210 thereby alerting the presence of water to any of those in the area.

The embodiment shown and described in FIGS. 18-21 is generally rectangular in shape and is preferably about 4.7 cm (1⅞" inch) wide, about 10 cm (4 inch) in length, and about 1.6 cm (⅝" inch) deep. However the dimensions may vary depending on a number of factors. The width may range from about 1.3 cm (0.5 inch) to about 20 cm (8 inch). The length, or height, may range from about 2.5 cm (1 inch) to about 40 cm (16 inch). The device may be about 0.64 cm (0.25 inch) to about 5 cm (2 inch) deep or thick.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A water leak warning device comprising:
    a rectangular hollow body having an interior space, the hollow body having rigid walls comprising at least a top wall, a bottom wall, and a plurality of side walls, wherein there is an adhesive disposed on at least one of the plurality of side walls;
    at least two electrodes each having a first end extending out of the bottom wall in a direction generally perpendicular to the bottom wall;
    a power supply enclosed in the interior space of the hollow body;
    a speaker enclosed in the interior space of the hollow body;
    an aperture traversing at least one of the plurality of the side walls,
       wherein the at least two electrodes, the power supply, and the speaker are operatively connected by conducting elements such that when the first end of each of the at least two electrodes are connected by a conductive material, an audible signal is emitted by the speaker through the aperture traversing the at least one side wall; and
    a reverberating chamber partially or wholly surrounding the aperture.

2. The water leak warning device of claim 1 wherein the plurality of side walls extend past the bottom wall.

3. The water leak warning device of claim 1 further comprising at least one air release hole in at least one of the plurality of sidewalls.

4. The water leak warning device of claim 1 wherein a width of the water leak warning device is about 1.3 cm to about 20 cm, a length of the water leak warning device is about 2.5 cm to about 40 cm, and a thickness of the water leak warning device is about 0.64 cm to about 5.0 cm.

5. The water leak warning device of claim 4 wherein the width is about 4.7 cm, the length is about 10 cm, and the thickness is about 1.6 cm.

6. The water leak waning device of claim 4 wherein a ratio of the length to the width is about 2:1.

7. The water leak warning device of claim 1 further comprising an indentation on at least one of the plurality of sidewalls,
    wherein the indentation permits an inlay to lie flush with the sidewall surface.

\* \* \* \* \*